United States Patent
Smith et al.

(10) Patent No.: US 10,882,229 B2
(45) Date of Patent: Jan. 5, 2021

(54) METHODS AND DEVICES FOR APPLYING BONE CEMENT TO ORTHOPEDIC PROSTHESES TO ENHANCE BOND STRENGTH

(71) Applicant: Biomet Manufacturing, LLC, Warsaw, IN (US)

(72) Inventors: Daniel B. Smith, Warsaw, IN (US); Timothy G Vendrely, Fort Wayne, IN (US); Tayler Kreider, Warsaw, IN (US); Imad K. Merkhan, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 160 days.

(21) Appl. No.: 15/942,823

(22) Filed: Apr. 2, 2018

(65) Prior Publication Data

US 2018/0290354 A1 Oct. 11, 2018

Related U.S. Application Data

(62) Division of application No. 14/117,482, filed as application No. PCT/US2012/037786 on May 14, 2012, now Pat. No. 9,944,000.

(Continued)

(51) Int. Cl.
*B29C 45/14* (2006.01)
*B29C 45/34* (2006.01)
(Continued)

(52) U.S. Cl.
CPC .... *B29C 45/14336* (2013.01); *A61B 17/8841* (2013.01); *A61F 2/3094* (2013.01);
(Continued)

(58) Field of Classification Search
CPC . B29C 45/7646; B29C 45/76; B29C 45/7207; B29C 45/72; B29C 45/78;
(Continued)

(56) References Cited

U.S. PATENT DOCUMENTS 3,417,175 A * 12/1968 Brown .............. B29C 45/14827
264/220
5,376,123 A 12/1994 Klaue et al.
(Continued)

FOREIGN PATENT DOCUMENTS

CA 2835030 9/2017
CN 2259270 Y 8/1997
(Continued)

OTHER PUBLICATIONS

"Chinese Application Serial No. 201710146359.3, Office Action dated Apr. 23, 2019", W/O English Translation, 13 pgs.
(Continued)

*Primary Examiner* — Philip C Tucker
*Assistant Examiner* — Jimmy R Smith, Jr.
(74) *Attorney, Agent, or Firm* — Schwegman Lundberg & Woessner, P.A.

(57) ABSTRACT

An apparatus for forming a flowable material against a prosthetic implant can comprise a mold body having an outer surface and an inner surface. The inner surface can define a mold cavity that is selectively configured to at least partially accept the prosthetic implant in a forming position. An inlet port can be configured on the mold cavity that extends between the inner and outer surfaces. The mold cavity can substantially conform to a profile of a bone opposing surface of the prosthetic implant such that a void is created between the inner surface of the mold body and the bone opposing surface of the prosthetic implant. The inlet port can be configured to permit introduction of the flowable material into the void and against the bone opposing surface of the prosthetic implant.

19 Claims, 15 Drawing Sheets

Related U.S. Application Data

(60) Provisional application No. 61/485,975, filed on May 13, 2011.

(51) Int. Cl.

| | |
|---|---|
| *B29C 45/26* | (2006.01) |
| *A61B 17/88* | (2006.01) |
| *A61F 2/30* | (2006.01) |
| *B29K 33/00* | (2006.01) |
| *B29L 31/00* | (2006.01) |

(52) U.S. Cl.
CPC .... *A61F 2/30942* (2013.01); *B29C 45/14827* (2013.01); *B29C 45/26* (2013.01); *B29C 45/34* (2013.01); *A61F 2002/30957* (2013.01); *A61F 2002/30963* (2013.01); *B29K 2033/12* (2013.01); *B29K 2901/12* (2013.01); *B29L 2031/7532* (2013.01); *F04C 2270/0421* (2013.01)

(58) Field of Classification Search
CPC . B29C 45/14827; B29C 45/03; B29C 45/036; B29C 45/1781; B29C 45/20; B29C 2045/202; B29C 2045/205; B29C 45/14336; B29C 2045/1477; B29C 2045/4068; B29L 2031/7532; A61B 17/8841; A61B 17/8833
USPC .................................. 156/242; 264/334, 338
See application file for complete search history.

(56) References Cited

U.S. PATENT DOCUMENTS

| | | | | |
|---|---|---|---|---|
| 6,361,731 | B1 * | 3/2002 | Smith ................. | A61F 2/30942 264/271.1 |
| 9,944,000 | B2 | 4/2018 | Smith et al. | |
| 2003/0009232 | A1 * | 1/2003 | Metzger ............... | A61F 2/3868 623/20.29 |
| 2009/0157189 | A1 | 6/2009 | Hartman et al. | |
| 2009/0175978 | A1 | 7/2009 | Hawkins et al. | |
| 2010/0102484 | A1 | 4/2010 | Haney et al. | |
| 2010/0152319 | A1 * | 6/2010 | Shalaby ............... | A61K 9/5026 523/117 |
| 2015/0343684 | A1 | 12/2015 | Smith et al. | |

FOREIGN PATENT DOCUMENTS

| | | |
|---|---|---|
| CN | 106974719 A | 7/2017 |
| DE | 4228317 A1 | 3/1994 |
| JP | 201207343 A | 3/2012 |
| JP | 6049703 B2 | 12/2016 |
| WO | WO-2010050995 A1 | 5/2010 |
| WO | WO-2012158618 A1 | 11/2012 |

OTHER PUBLICATIONS

"Chinese Application Serial No. 201710146359.3, Response filed Jun. 13, 2019 to Office Action dated Apr. 23, 2019", w/o English claims, 8 pgs.
"Chinese Application Serial No. 201710146359.3, Office Action dated Nov. 22, 2018", w/ English translation, 21 pgs.
"Chinese Application Serial No. 201710146359.3, Response Filed Mar. 29, 2019 to Office Action dated Nov. 22, 2018", w/English Claims, 18 pgs.
"U.S. Appl. No. 14/117,482, Notice of Allowance dated Dec. 14, 2017", 10 pgs.
"U.S. Appl. No. 14/117,482, Preliminary Amendment filed Aug. 29, 2017", 9 pgs.
"U.S. Appl. No. 14/117,482, Preliminary Amendment filed Nov. 13, 2013", 9 pgs.
"U.S. Appl. No. 14/117,482, Response filed Nov. 13, 2017 to Restriction Requirement dated Sep. 26, 2017", 7 pgs.
"U.S. Appl. No. 14/117,482, Restriction Requirement dated Sep. 26, 2017", 6 pgs.
"Australian Application Serial No. 2012255975, First Examiner Report dated Oct. 18, 2015", 2 pgs.
"Australian Application Serial No. 2012255975, Response filed Feb. 12, 2016 to First Examiner Report dated Oct. 18, 2015", 16 pgs.
"Chinese Application Serial No. 2012800234978, Office Action dated Apr. 7, 2015".
"Chinese Application Serial No. 2012800234978, Office Action dated May 12, 2016", w/English Translation; 10 pgs.
"Chinese Application Serial No. 2012800234978, Office Action dated Nov. 30, 2015", w/English Translation, 12 pgs.
"Chinese Application Serial No. 2012800234978, Response filed Jan. 29, 2016 to Office Action dated Nov. 30, 2015", w/ English Translation, 6 pgs.
"Chinese Application Serial No. 2012800234978, Response filed Jul. 14, 2016 to Office Action dated May 12, 2016", w/ English Claims, 16 pgs.
"Chinese Application Serial No. 2012800234978, Response filed Sep. 8, 2015 to Office Action dated Apr. 7, 2015", w/ English Claims, 11 pgs.
"Chinese Application Serial No. 2012800234978, Voluntary Amendment filed Jul. 10, 2014", w/ English Claims, 10 pgs.
"European Application Serial No. 14172750.3, Communication Pursuant to Article 94(3) EPC dated Nov. 14, 2016", 4 pgs.
"European Application Serial No. 14172750.3, Extended European Search Report dated Aug. 25, 2014", 6 pgs.
"European Application Serial No. 12723043.1, Response filed Apr. 7, 2017 to Office Action dated Dec. 5, 2017", 12 pgs.
"European Application Serial No. 12723043.1, Response filed Jun. 17, 2014 to Office Action dated Jan. 22, 2014", 10 pgs.
"European Application Serial No. 14172750.3, Response filed Feb. 20, 2015 to Office Action dated Aug. 25, 2014", 21 pgs.
"European Application Serial No. 14172750.3, Response filed Mar. 24, 2017 to Office Action dated Nov. 14, 2016", 22 pgs.
"International Application Serial No. PCT/US2012/037786, International Preliminary Report on Patentability dated Oct. 21, 2013", 23 pgs.
"International Application Serial No. PCT/US2012/037786, International Search Report dated Jul. 30, 2012", 4 pgs.
"International Application Serial No. PCT/US2012/037786, Written Opinion dated Jul. 30, 2012", 6 pgs.
"Japanese Application Serial No. 2014-510539, Office Action dated Mar. 11, 2016", W/ English Translation, 5 pgs.
"Japanese Application Serial No. 2014-510539, Response filed Jun. 13, 2016 to Office Action dated Mar. 11, 2016", w/ English Claims, 12 pgs.
"European Application Serial No. 14172750.3, Communication Pursuant to Article 94(3) EPC dated Nov. 8, 2018", 5 pgs.

* cited by examiner

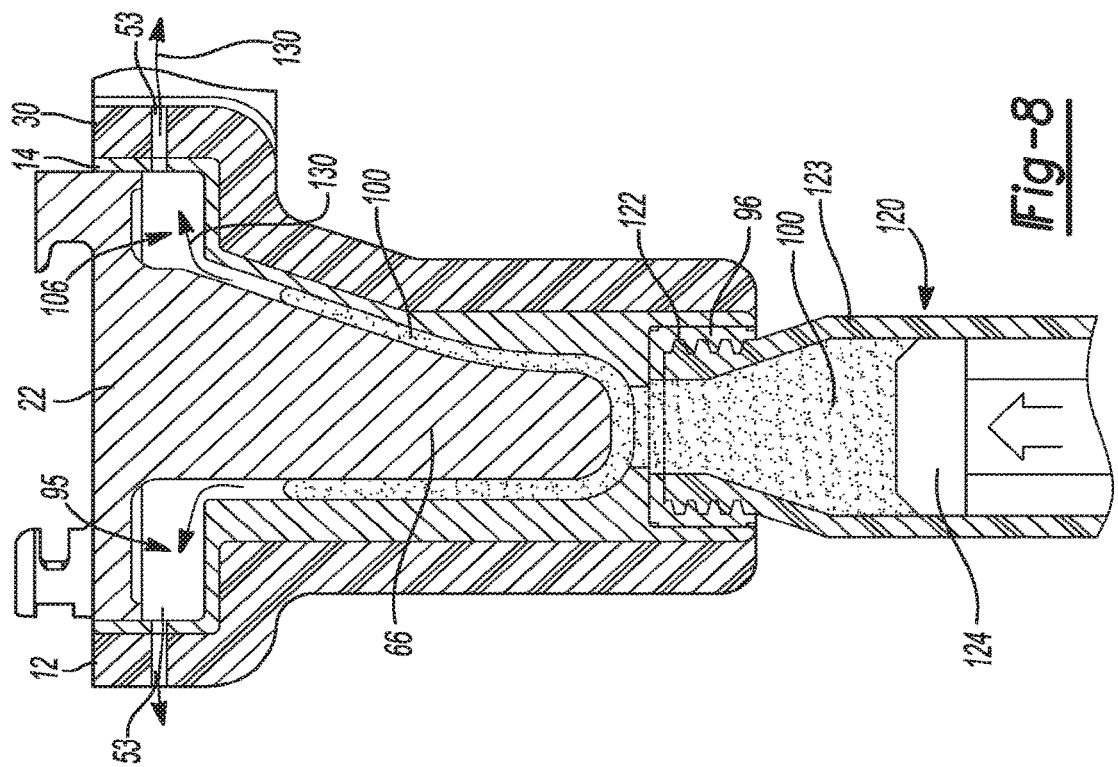
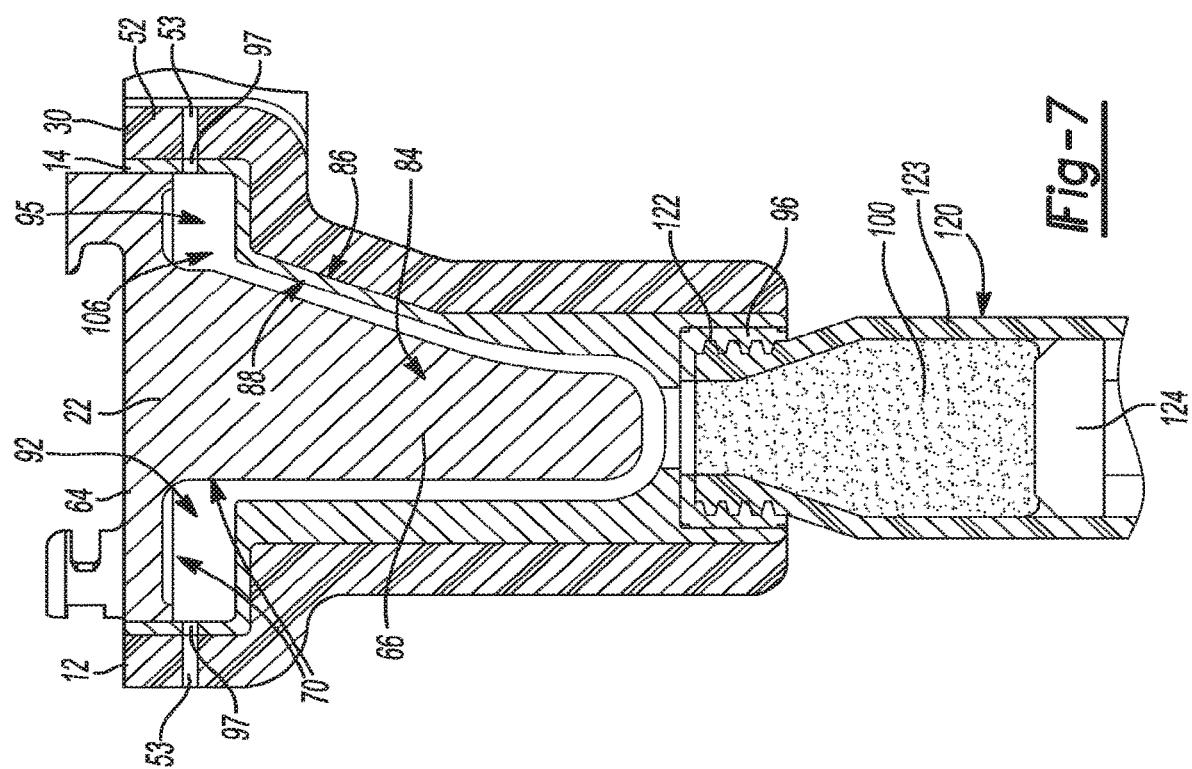

METHODS AND DEVICES FOR APPLYING BONE CEMENT TO ORTHOPEDIC PROSTHESES TO ENHANCE BOND STRENGTH

The present disclosure relates generally to orthopedic implants that incorporate bone cement between the implant and the opposing bone surface, and more specifically, to a mold body and related method for forming a flowable material against the orthopedic implant prior to implantation.

In many examples, it may be desirable to incorporate bone cements such as polymethyl-methacrylate (PMMA) between the bone opposing surface of the implant and the host bone. In this regard, such bone cements can offer an adhesive property to further couple the implant to the host bone. Cement bond strength can be a function of both true adhesion and micro-mechanical interlock that can be established between the cement and the bone opposing surface of the implant (in some examples such as a grit-blasted or porous metal surface). Micro-mechanical interlock is influenced significantly by cement viscosity, with very high viscosity cements lacking the ability to establish a superior micro-mechanical interlock. Both pre-dough or doughy cement surfaces that have been exposed to air for a period of time can form a leathery skin via monomer liquid evaporation. These leathery surfaces can be especially poorly suited to forming a good micro-mechanical interlock and therefore, may possess virtually no adhesive properties.

Bone cement can sometimes be applied to a prepared bone at the implantation site first. Sometimes, bone cement may be applied to the implant prior to placing it. Other times, a combination of these cement application methods may be used. In the interest of time and minimizing mess, it can be advantageous to use doughy cement regardless of the technique employed. However, the use of very doughy cement, and especially cement on which a leathery skin has formed, can result in sub-optimal cement-prosthesis interface quality. Application of low viscosity or medium viscosity cement directly to implants is not practical as it typically runs off of the implant. As a result, a surgeon must try to balance time, mess, and interface quality.

SUMMARY

This section provides a general summary of the disclosure, and is not a comprehensive disclosure of its full scope or all of its features.

An apparatus for forming a flowable material against a prosthetic implant can comprise a mold body having an outer surface and an inner surface. The inner surface can define a mold cavity that is selectively configured to at least partially accept the prosthetic implant in a forming position. In some embodiments, an inlet port is configured on the mold cavity that extends between the inner and outer surfaces. The mold cavity can substantially conform to a profile of a bone opposing surface of the prosthetic implant (i.e., the surface of the implant which is facing, but not necessarily in direct contact with the bone) such that a void is created between the inner surface of the mold body and the bone opposing surface of the prosthetic implant. The inlet port can be configured to permit introduction of the flowable material into the void and against the bone opposing surface of the prosthetic implant.

According to other features, the mold body can further define at least one vent formed through the inner and outer surfaces. The vent can be configured to permit air to escape therethrough upon the introduction of the flowable material into the void. The mold body can be formed of a rigid material. In one example, the mold body can be formed of silicone material.

According to still other features, the apparatus can further include a membrane that is removably disposed on the inner surface of the mold cavity. The membrane can be flexible. The membrane can comprise at least one of a slit, thin section, perforations, and a tear starting notch. The membrane can be formed of silicone.

The mold cavity can further comprise a first cavity portion having a geometry that corresponds to a first feature of the prosthetic component and a second cavity portion having a geometry corresponding to a second feature of the prosthetic component. The prosthetic component can comprise a tibial tray. The first feature can comprise a platform portion of the tibial tray. The second feature can comprise a stem of the tibial tray. At least one of the mold body and membrane can include a vacuum port formed therethrough.

A kit for forming a flowable material against a prosthetic implant can include a prosthetic component having a bone opposing surface. The kit can further comprise a mold body having an outer surface and an inner surface. The inner surface can define a mold cavity that is selectively configured to at least partially accept the prosthetic implant in a forming position. An inlet port can be configured on the mold body that extends between the inner and outer surfaces. The mold cavity can substantially conform to a profile of the bone opposing surface of the prosthetic implant such that a void is created between the inner surface of the mold body and the bone opposing surface of the prosthetic implant.

A method for forming a flowable material against a prosthetic implant can comprise locating the prosthetic implant at least partially into a mold cavity thereby creating a void between a bone opposing surface of the prosthetic implant and an inner surface of the mold cavity. The flowable material having a first viscosity can be introduced into the void and against the bone opposing surface of the prosthetic implant. A predetermined amount of time is allowed to pass until the flowable material has adhered to the bone opposing surface of the prosthetic implant and has a second viscosity that is higher than the first viscosity. The flowable material in the second viscosity can have a doughy texture. The prosthetic implant with the flowable material having the doughy texture adhered to the bone opposing surface can then be removed from the mold cavity.

The prosthetic implant can be located at least partially into the mold cavity by positioning a membrane intermediate the inner surface of the mold cavity and the bone opposing surface of the prosthetic implant. The method can further comprise coupling a flowable material delivery device to an inlet port on the mold body. The method can further include actuating the flowable material delivery device thereby introducing the flowable material having the first viscosity into the void and against the bone opposing surface of the prosthetic implant. During introduction of the flowable material, air can be released from the void through vent ports formed through the mold body during the introduction of the flowable material. The method can further include peeling the membrane from the flowable material having the second viscosity subsequent to removing the prosthetic implant and flowable material having the doughy texture from the mold cavity.

According to some features, introducing the flowable material having the first viscosity can comprise introducing the flowable bone cement against a bone opposing surface of a tibial component. Locating the prosthetic implant at least partially into a mold cavity can further comprise locating a platform portion of the tibial component into a first cavity portion of the mold cavity and locating a tibial stem of the tibial component into a second cavity portion of the mold cavity.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 7-9 illustrate an exemplary sequence of introducing a flowable material into a void created between the prosthetic implant and the membrane.

Corresponding reference numerals indicate corresponding parts throughout the several views of the drawings.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

Figure 1:
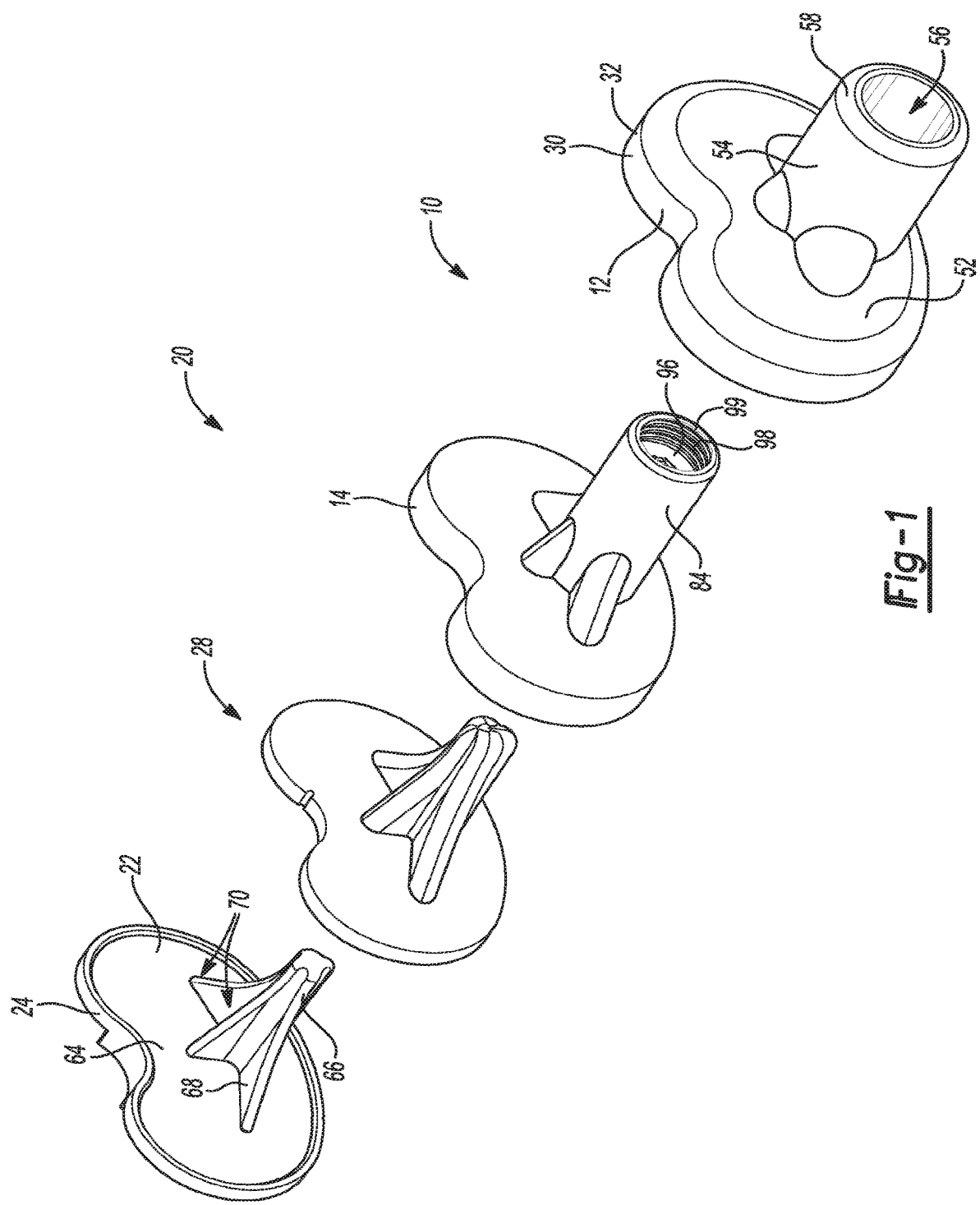
FIG. 1 is a perspective view of an exemplary kit constructed in accordance to the present teachings that includes a prosthetic implant, a dough-like structure, a membrane, and a mold.
Figure 2:
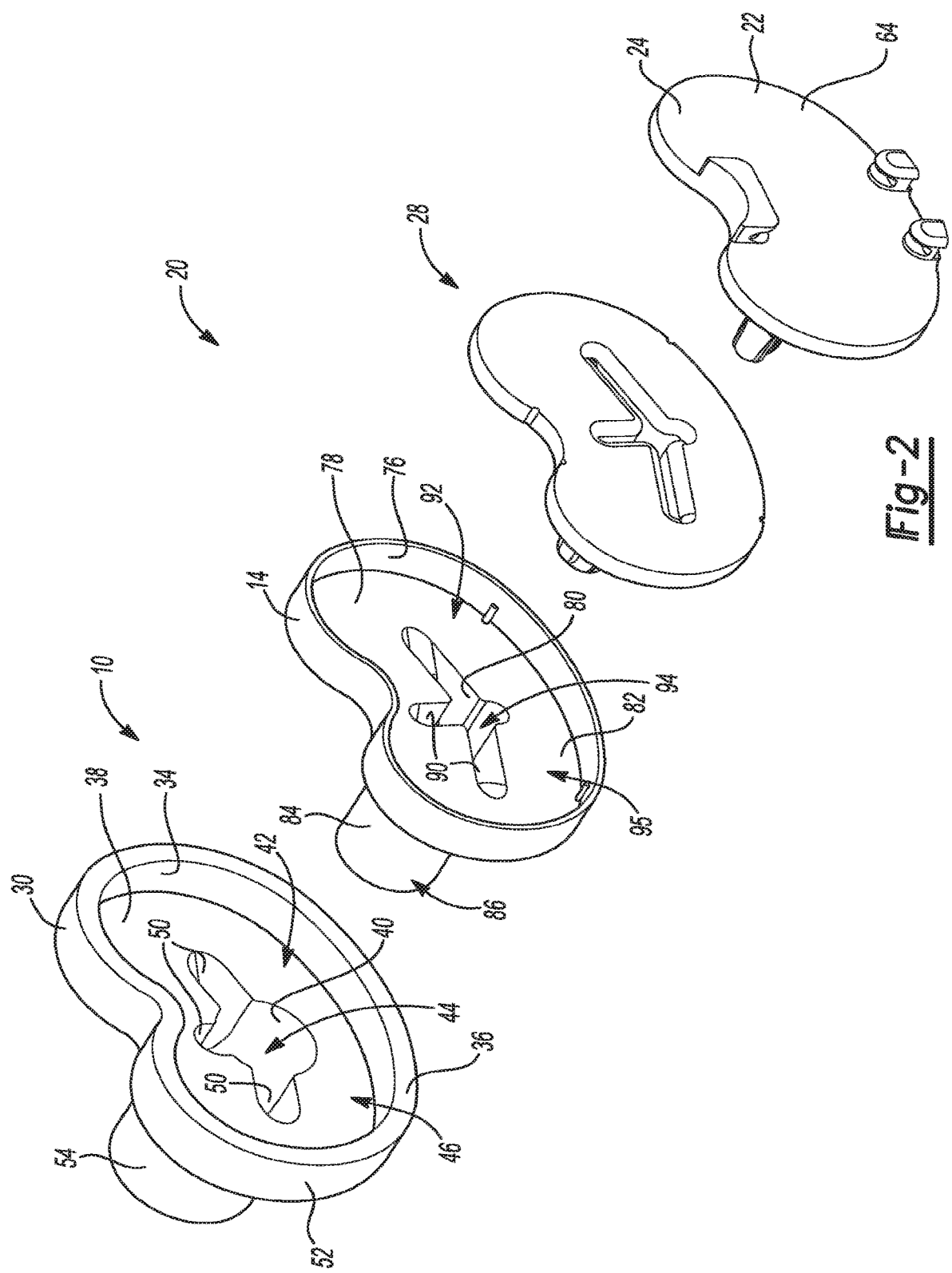
FIG. 2 is a perspective view of the kit of FIG. 1.
Figure 3:
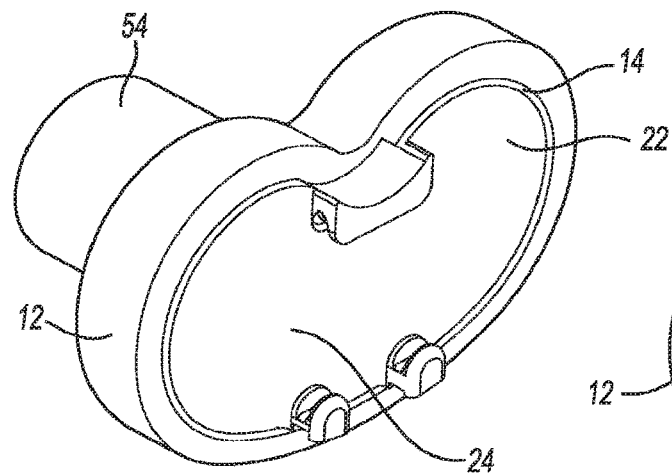
FIG. 3 is a perspective view of the prosthetic implant and membrane shown received into a cavity of the mold.
Figure 4:
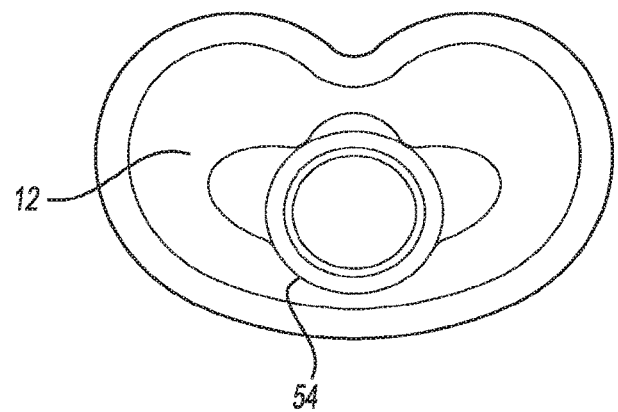
FIG. 4 is a bottom plan view of the mold of FIG. 1.
Figure 5:
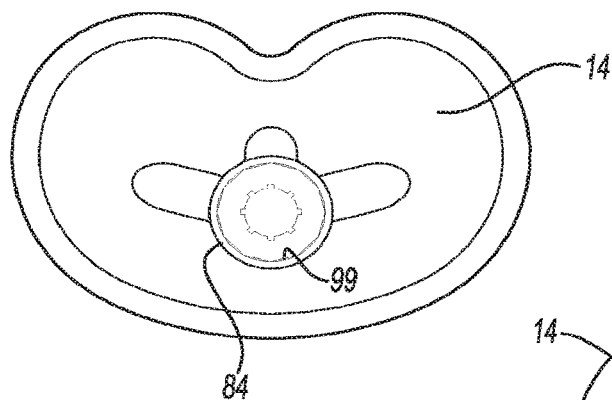
FIG. 5 is a bottom plan view of the membrane of FIG. 1.
Figure 6:
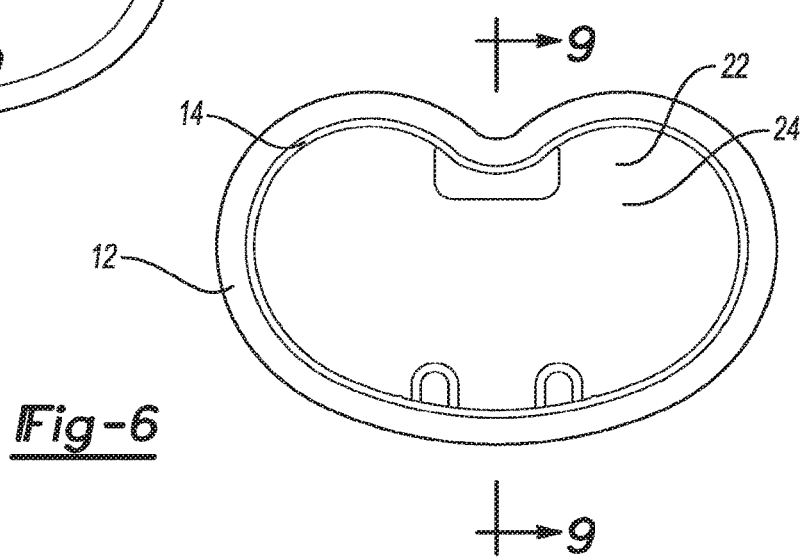
FIG. 6 is a top plan view of the prosthetic implant, membrane, and mold of FIG. 3.

With initial reference to FIGS. 1 and 2, an exemplary apparatus for forming a flowable material against a prosthetic implant is shown and generally identified at reference numeral 10. The flowable material described herein is bone cement such as, but not limited to, polymethylmethacrylate (PMMA bone) cement. Bone cements include those formed from a methyl methacrylate monomer and poly (methyl methacrylate) or methyl methacrylate-styrene homo- or copolymer. Such cements are generally made from mixing two components, usually during the clinical procedure, resulting in a composition which hardens over time. The cement components may comprise a powder component, comprising a polymer selected from homopolymers or copolymers of acrylic acid esters, methacrylic acid esters, styrene, vinyl derivatives, and mixtures thereof. The cement components may further comprise a reactive liquid comprising reactive organic monomers selected from methylmethacrylate, homolog esters of methacrylic acid or their mixtures. Cements among those useful herein include Palacos R, Cobalt HV, SmartSet HV, Simplex P, Cobalt MV, and SmartSet MV.

The apparatus 10 can generally include a mold 12 and a membrane 14. According to some examples as discussed herein, the apparatus 10 can be provided as part of a kit 20 that can further include a prosthetic implant 22. The prosthetic implant 22 discussed herein includes a tibial component 24. It will be appreciated however, that the various features and methods disclosed herein may be also used for forming a flowable material against other prosthetic implants such as knee femoral and patellar components, hip stems, acetabular cups, glenoid components, ulnar components, and other prosthetic implants that may require the use of bone cement between a bone opposing surface of the prosthetic implant and the corresponding bone surface of the host bone. As will become appreciated from the following discussion, the apparatus 10 can be used to introduce a flowable material (such as bone cement) having a first viscosity to a location against the prosthetic implant 22. The mold 12 and in some examples, together with the membrane 14, can cooperate to form the flowable material into a doughy cement or dough-like structure generally identified at reference numeral 28. The dough-like structure 28 is illustrated in exploded view simply for illustration purposes with the understanding that the dough-like structure 28 will have a second viscosity, greater than the first viscosity and be adhered to or otherwise coupled to the tibial component 24.

With continued reference now to FIGS. 1 and 2, additional features of the mold 12 will now be described. The mold 12 can generally comprise a mold body 30 having an outer surface 32 and an inner surface 34. The mold body 30 can generally include a perimeter wall 36, an end wall 38, and an elongated wall 40. The perimeter wall 36 and the end wall 38 can cooperate to define a first cavity portion 42. Similarly, the elongated wall 40 can define a second cavity portion 44. The first cavity portion 42 and the second cavity portion 44 can collectively define a mold cavity 46 of the mold body 30.

The elongated wall 40 can generally include fin receiving extension walls 50. As will become appreciated, the first cavity portion 42 can have a geometry that substantially conforms to a tray portion of the tibial component 24. Similarly, the second cavity portion 44 can generally provide a geometry that substantially conforms to a stem extending from the tibial component 24. The perimeter wall 36 and the end wall 38 can cooperate to form a tray receiving portion 52. Vent ports 53 (FIG. 7) can be formed through the mold body 30.

The elongated wall 40 can provide a stem receiving portion 54. An inlet port 56 can be formed on a distal end 58 of the stem receiving portion 54. In various examples, the mold body 30 can be formed of a rigid material, i.e., a material having sufficient rigidity to contain and define the cement material in a pre-determined shape forming a void around at least a portion of an implant, as further described below. Preferably, the material is transparent or translucent. Suitable materials include polyethylene, polycarbonate, polyethylene terephthalate (PET), and polypropylene. In various embodiments, the mold comprises polyethylene or polycarbonate.

The tibial component 24 can generally include a platform-like tray 64 and a stem 66. The stem 66 can comprise a series of fins 68 extending therefrom. The outer surface of the stem 66 and an underside surface of the platform-like tray 64 can collectively provide a bone opposing surface 70. Again it will be appreciated that the particular geometry of the tibial component 24 is merely exemplary.

The membrane 14 can generally include a perimeter wall 76, an end wall 78, and an elongated wall 80. The membrane 14 can further include a tray receiving portion 82 and a stem receiving portion 84. The stem receiving portion 84 can have an outer wall 86 and an inner wall 88 (FIG. 7). The elongated wall 80 can provide fin receiving extension walls 90. The perimeter wall 76 and the end wall 78 can collectively define a first cavity portion 92. The elongated wall 80 can define a second cavity portion 94. The first and second cavity portions 92 and 94 can cooperate to define an implant receiving cavity 95. Vent ports 98 (FIG. 7) can be formed through the membrane 14. In some examples, the vent ports 98 can be located for aligning with the vent ports 53 (FIG. 7) in the mold body 30.

An inlet port 96 can be provided on the stem receiving portion 84 of the membrane 14. The inlet port 96 in the examples shown generally comprises female threads 98. Anti-rotation facets 99 can be formed on the inlet port 96. It will be understood, however, that the inlet port 96 can additionally or alternatively include other mounting structures suitable to couple with a full material delivery device. Furthermore, it will be appreciated that while the threads 98 have been shown associated with the membrane 14, threads may additionally or alternatively be formed on the mold body 30 at the inlet port 56. In such a configuration the mold 12 could be used without the membrane 14.

The membrane 14 can be formed of a generally flexible material such as silicone. The membrane 14 can be removably disposed on the inner surface 34 of the mold cavity 46. In this regard, the membrane 14 can be thin, flexible, and freely cement-releasing. The membrane 14 can include features to allow for easy separation from the doughy cement 28, such as thin sections, fine perforations, and/or a tear starting notch or cut. The membrane 14 can have a low tear strength such as some silicone formulations. While not specifically shown, a vacuum port may be included in one or both of the mold 12 and membrane 14 to further improve the quality of the prosthesis-cement interface by eliminating or minimizing porosity at the prosthesis-cement interface. The vacuum port can also result in easier cement delivery, and reduced bone cement monomer vapors in the operating room environment.

In other embodiments, the mold 12 may be in the form of an open-topped mold/shell that cement in a pre-dough state, and/or in a reduced viscosity state could be delivered into. The prosthetic implant 22 could be introduced to the tacky cement via the open top resulting in a geometry equivalent to, or several millimeters thicker than, that of the desired final cement mantle.

Figure 9:
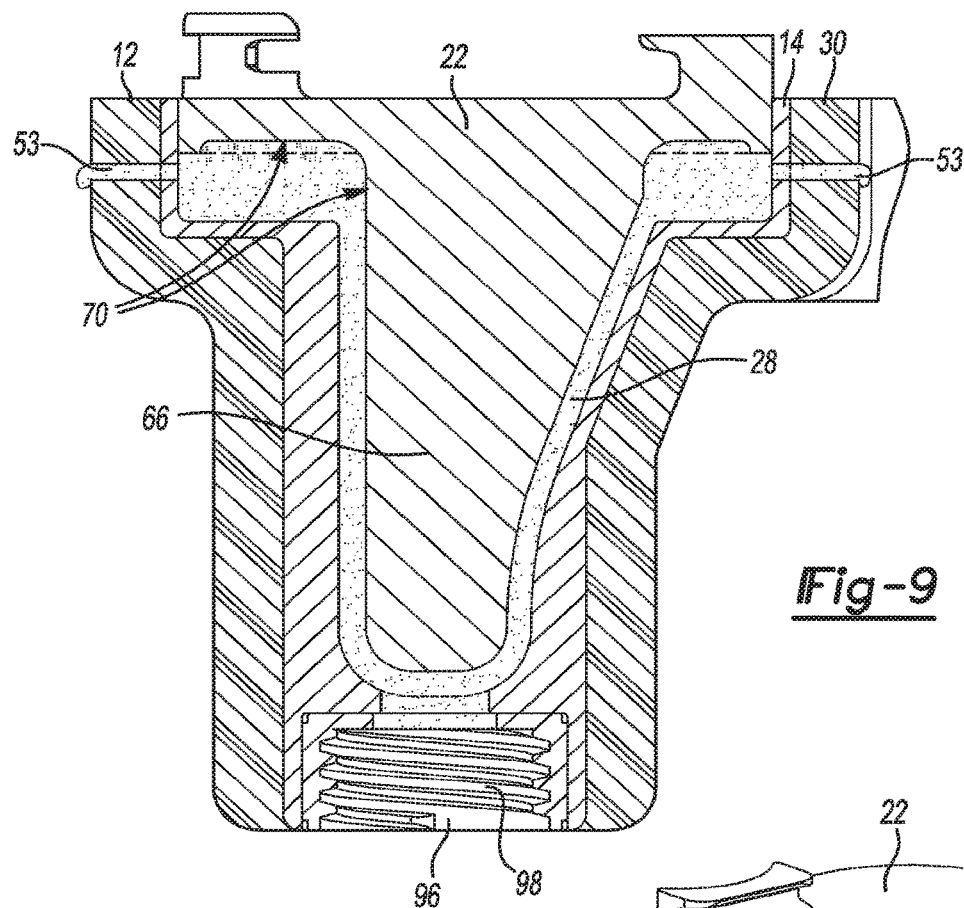

With particular reference now to FIGS. 7-9, an exemplary method of forming a flowable material 100 against the prosthetic implant 22 will be described. At the outset, the prosthetic implant 22 can be located generally into the implant receiving cavity 95 of the membrane 14. Once the prosthetic implant 22 has been sufficiently received into the implant receiving cavity 95, a void 106 can be created generally between the bone opposing surface 70 of the prosthetic implant 22 and the inner wall 88 of the membrane 14. In the position shown in FIG. 7, the stem 66 is received at least partially by the stem receiving portion 84 of the membrane 14. Similarly, the platform-like tray 64 is at least partially received by the first cavity portion 92 of the membrane 14.

It will be appreciated that the void 106 will be of a size and shape that will determine the shape and dimensions of the cement mantle applied to the implant 22 prior to implantation. In various embodiments, the shape of the void, and resulting mantle, will substantially conform to the profile of the implant. It is understood, though, that the dimensions of the void and resulting mantle may vary in along the surface of the implant. In general, the void and resulting mantle may be from about 1 mm to about 15 mm, from about 2 mm, from about 10 mm, or from about 3 to about 7 mm, in depth. In embodiments with a first and second cavity portions, as discussed above, the void and resulting mantle in the first cavity portion may differ in dimension from the void and resulting mantle in the second cavity portion. For example, when the second cavity portion defines a stem, the void and resulting mantle in the second cavity portion may have a depth greater than that of the void and resulting mantle in the first cavity portion.

Next, a surgeon can couple a flowable material delivery device 120 generally to the inlet port 96 on the membrane 14. In the example shown, the flowable material delivery device 120 generally includes male threads 122 that can be configured to threadably mate with the threads 98 provided on the inlet port 96 of the membrane 14. Other configurations are contemplated. In one example, the flowable material delivery device 120 can be, or incorporate features of, an Optivac® vacuum mixing system offered by Biomet Manufacturing Corp. of Warsaw, Ind.

The exemplary flowable material delivery device 120 can generally include a syringe portion 123 and a plunger portion 124. Next, a surgeon can retain the prosthetic implant 22 generally within the implant receiving cavity 95 such as by a finger or other retaining measure. It is contemplated that the perimeter wall 36 of the mold body 30 can have an overhanging lip that may be flexibly retain the tibial component 24 within the implant receiving cavity 95. Nevertheless, once the prosthetic implant 22 is suitably retained within the implant receiving cavity 95, a surgeon can depress the plunger 124 causing the flowable material (i.e., bone cement) 100, still in a relatively low viscosity state, through the inlet port 56 of the mold body 30, and through the inlet port 96 of the membrane 14 and into the void 106 (see FIG. 8).

During advancement of the flowable material 100 into the void 106, air 130 that was present within the void 106 can be urged through the respective vents 98 and 53. Injection of the flowable material 100 is continued until a suitable amount of flowable material 100 has been deployed. It is contemplated, that in some examples, the flowable material 100 can be continued to be advanced into the void 106 until the surgeon observes flowable material 100 being expelled through the ports 53. In this regard, the surgeon continues the introduction of the flowable material 100 such that the flowable material 100 is sufficiently located in contact with the bone opposing surface 70 of the prosthetic implant 22.

The surgeon may then decouple the flowable material delivery device 120 from the inlet port 96 as shown in FIG. 9. The surgeon can then wait a predetermined amount of time until the flowable material reaches a suitable viscosity (higher than the viscosity of the flowable material 100 during introduction into the void 106) has been reached. It will be appreciated that the viscosity will vary over time, subject to the composition of the flowable material (e.g., composition of the cement) and curing conditions (e.g., temperature). The predetermined time may be any time acceptable in clinical practice, and may depend on such factors as the composition of the flowable material (e.g., cement), the implant, the condition of the bone into which the implant is to be inserted, and surgical clinical conditions and procedures. In some embodiments, wherein a cement having a relatively high viscosity is used, the predetermined time is from about 1 to about 3 minutes after initial mixing of cement components and injection into the mold. In general, the viscosity after the predetermined time will approximate a dough, which is not substantially flowable, but is deformable with application of pressure by manual manipulation of the material, which may be aided using tools and devices, consistent with acceptable clinical practice.

Figure 10:
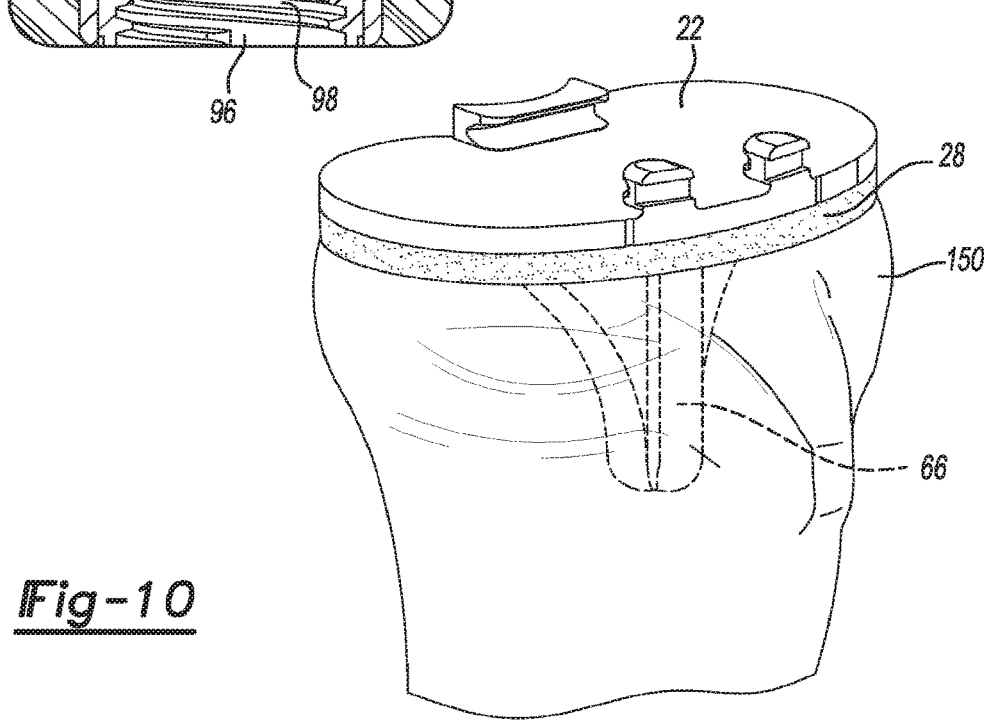
FIG. 10 is an anterior perspective view of an exemplary tibia of which the prosthetic implant and resulting dough-like structure are implanted.
Figure 11:
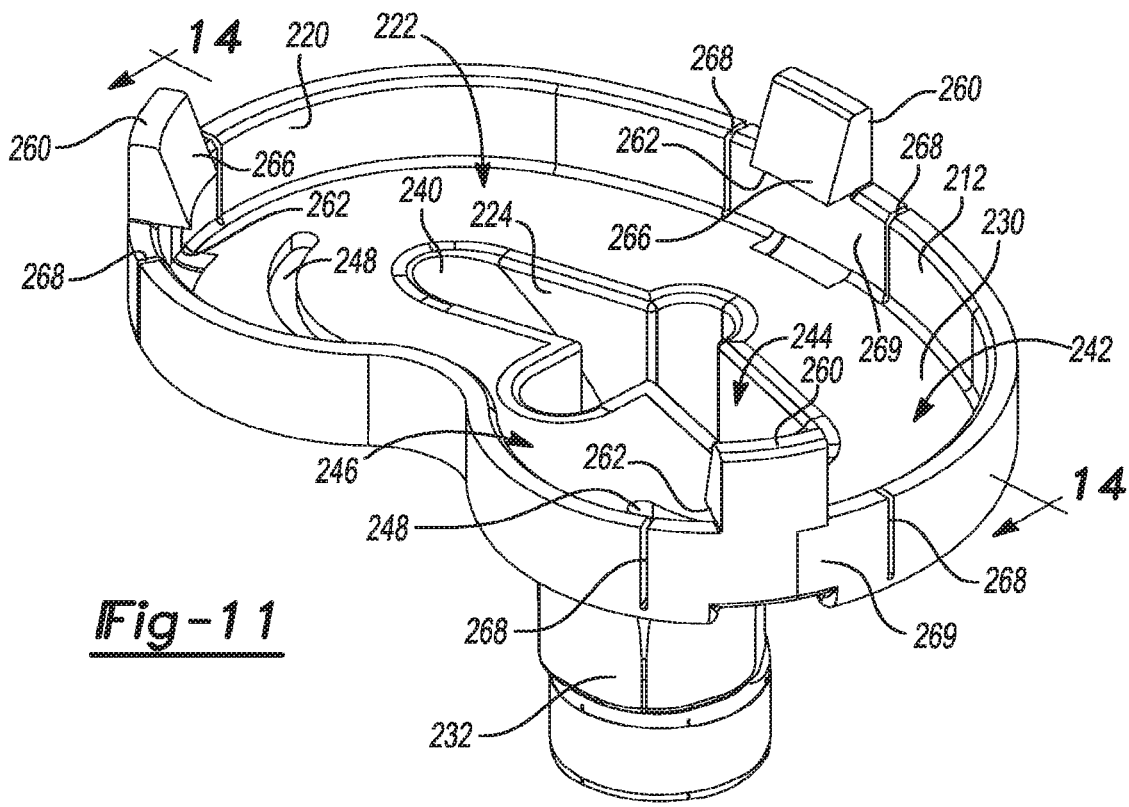
FIG. 11 is a top perspective view of a mold constructed in accordance with additional features of the present disclosure.
Figure 12:
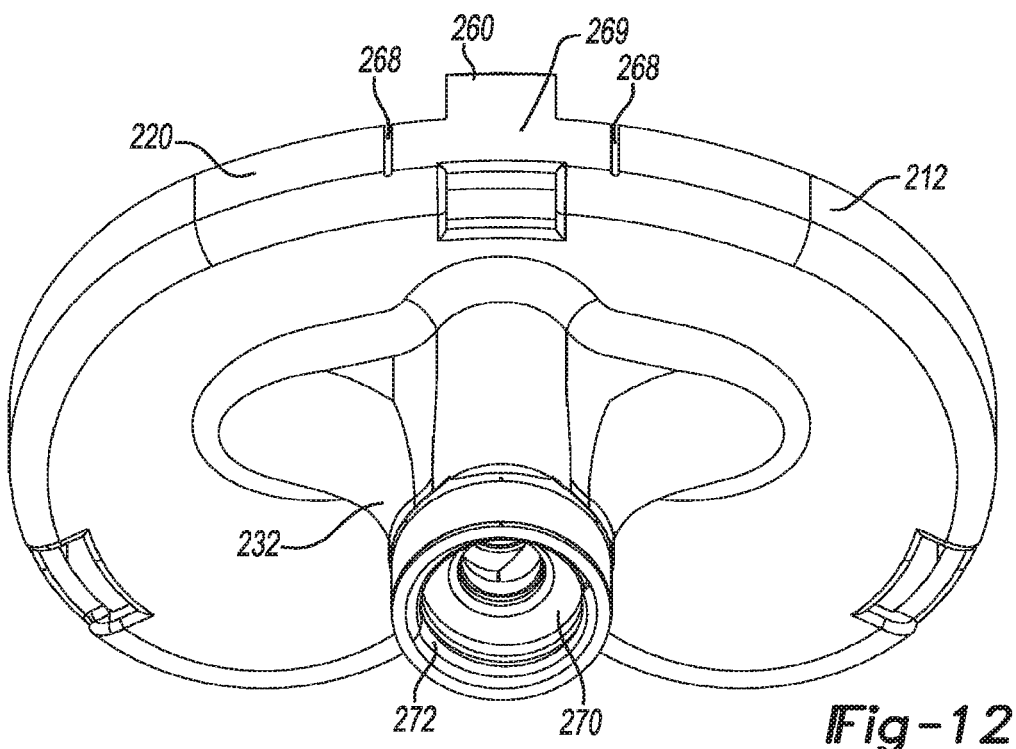
FIG. 12 is a bottom perspective view of the mold of FIG. 11.
Figure 13:
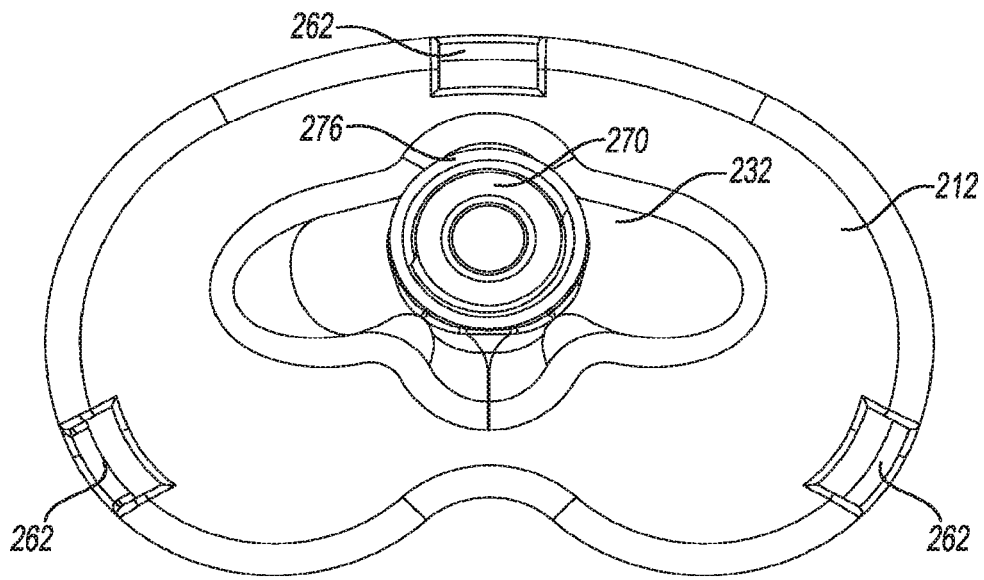
FIG. 13 is a bottom plan view of the mold of FIG. 11.
Figure 14:
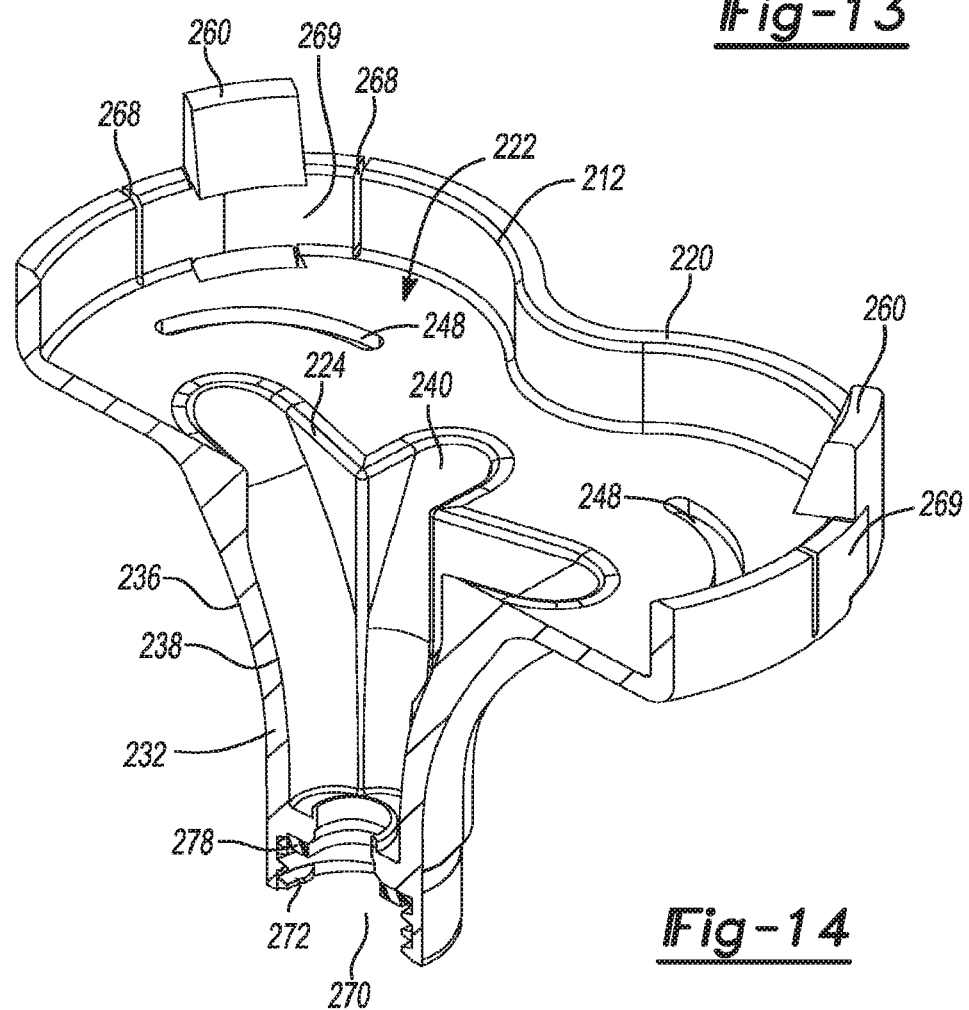
FIG. 14 is a sectional view taken along lines 14-14 of FIG. 11.
Figure 15:
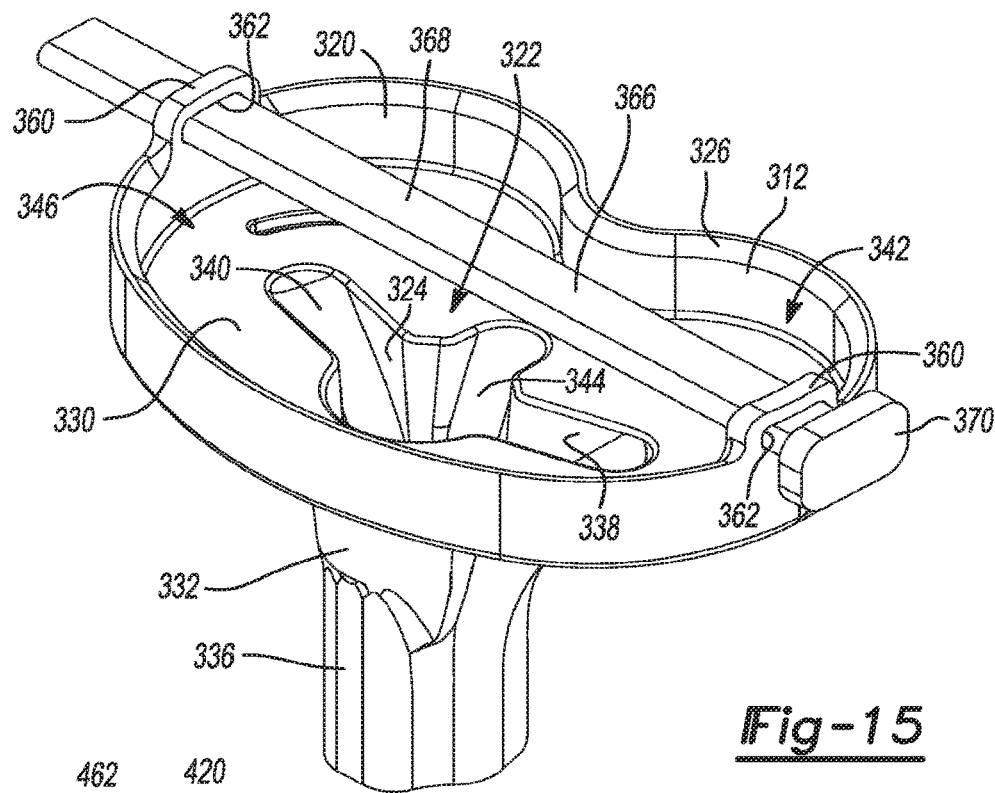
FIG. 15 is a top perspective view of a mold constructed in accordance with additional features of the present disclosure.
Figure 16:
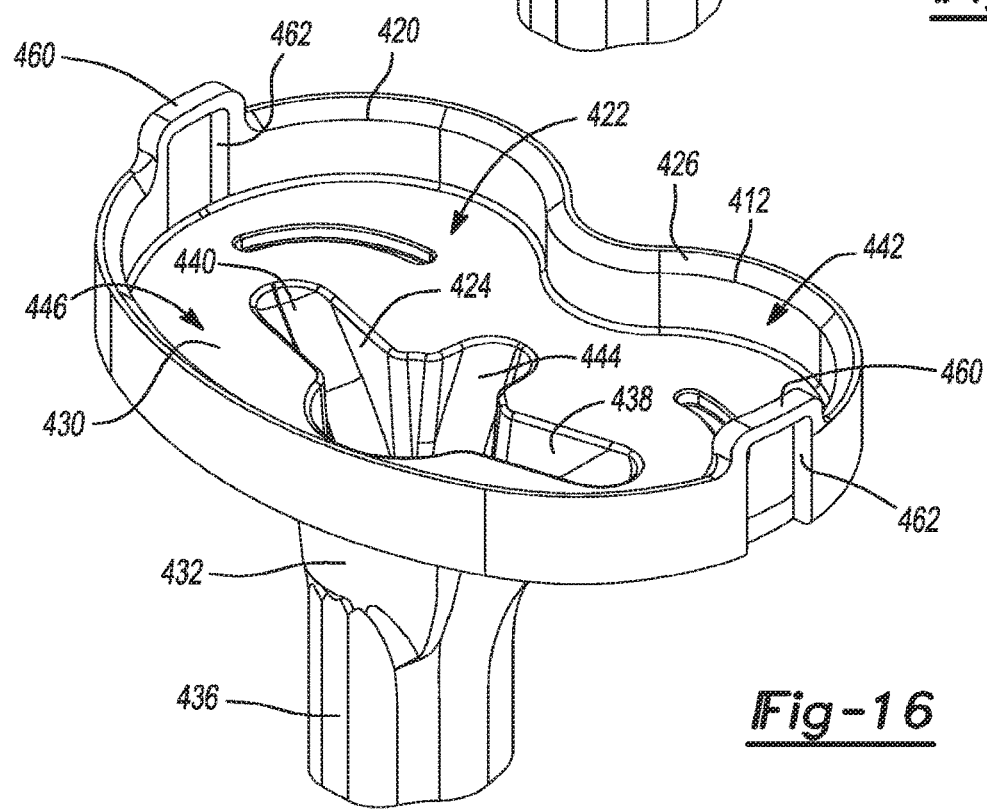
FIG. 16 is a top perspective view of a mold constructed in accordance with additional features of the present disclosure
Figure 17:
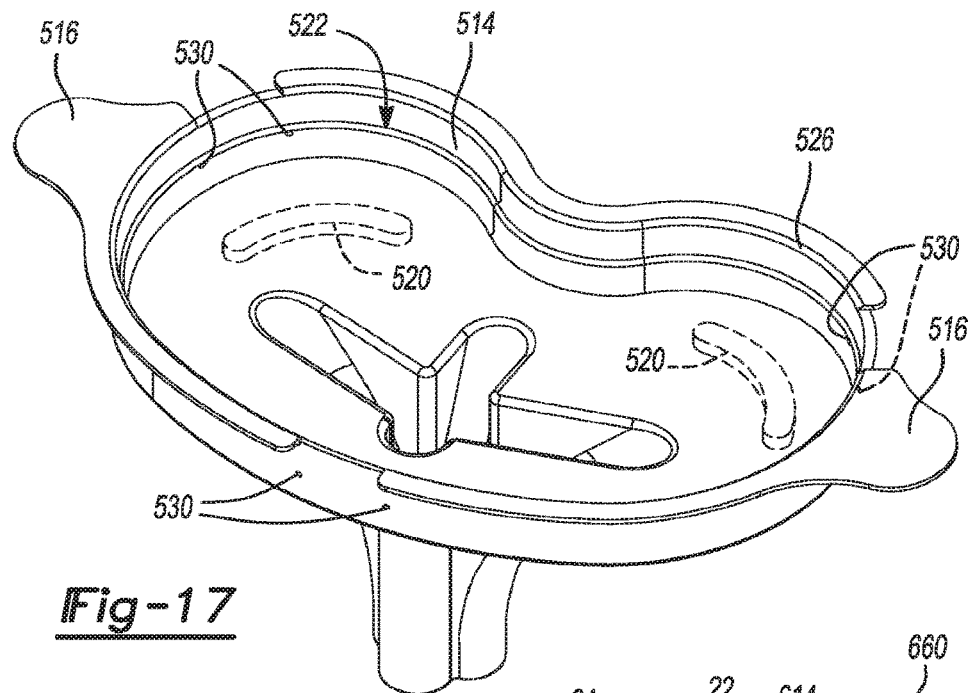
FIG. 17 is a front perspective view of a membrane according to additional features of the present disclosure.
Figure 18:
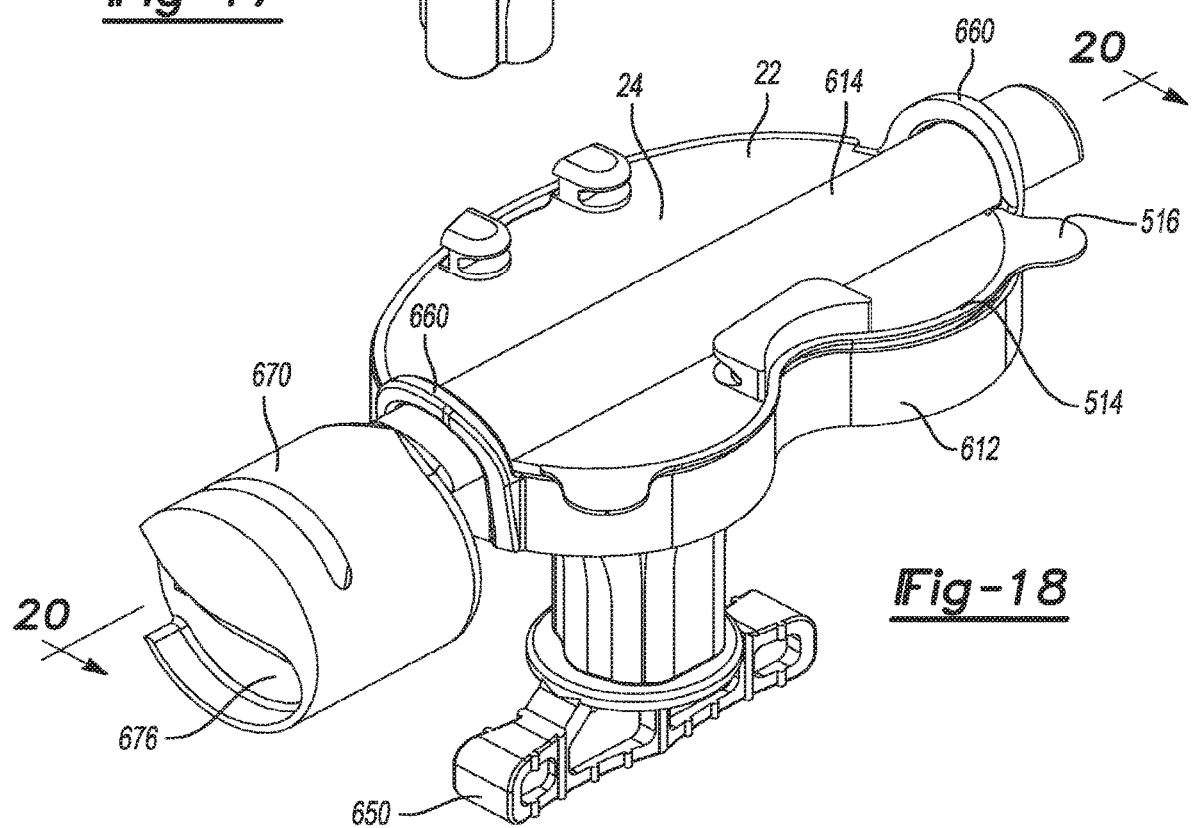
FIG. 18 is a perspective view of an exemplary mold and a locking bar according to other features of the present disclosure.
Figure 19:
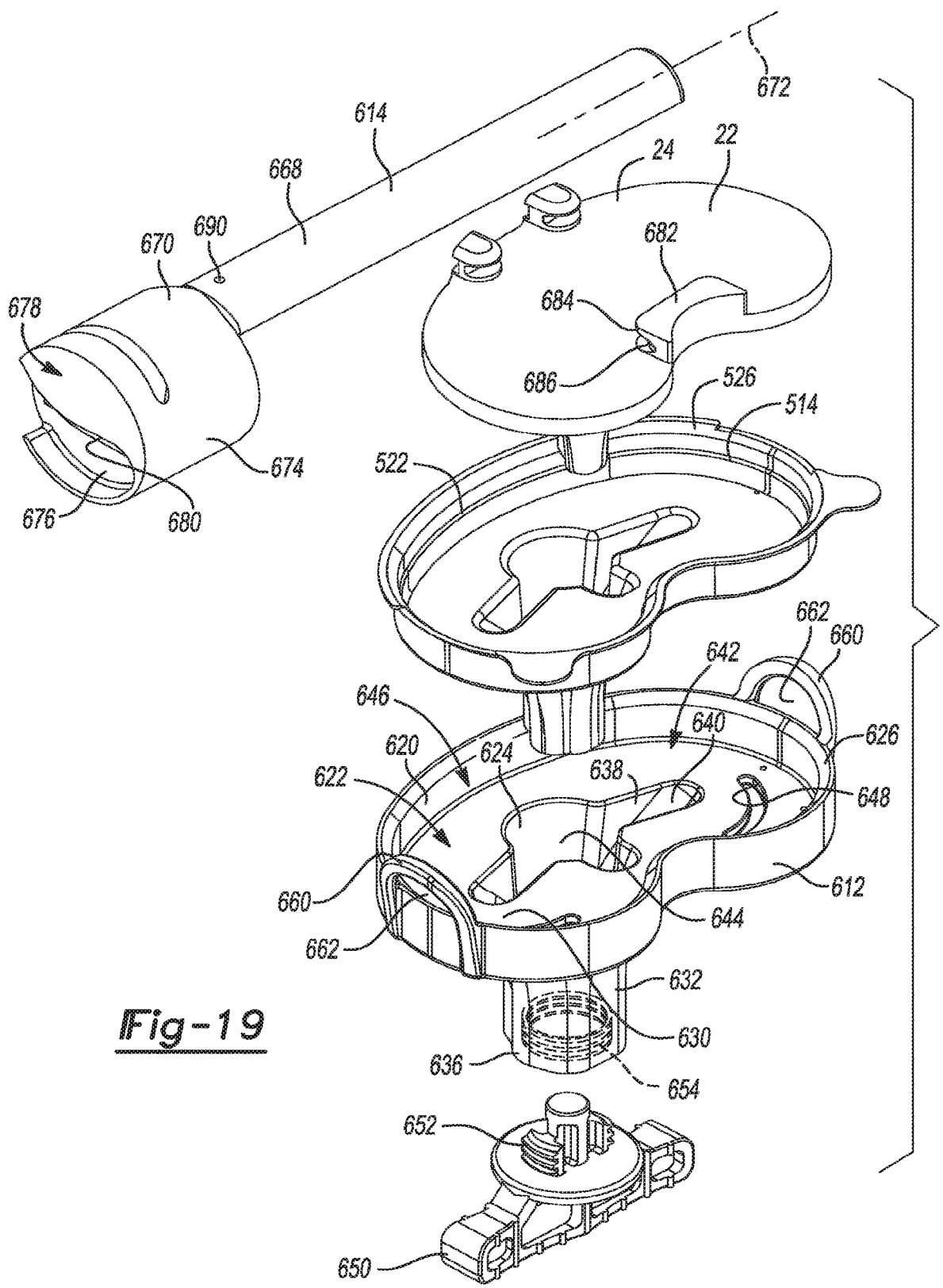
FIG. 19 is an exploded perspective view of the mold, locking bar, tibial component and membrane of FIG. 18.
Figure 20:
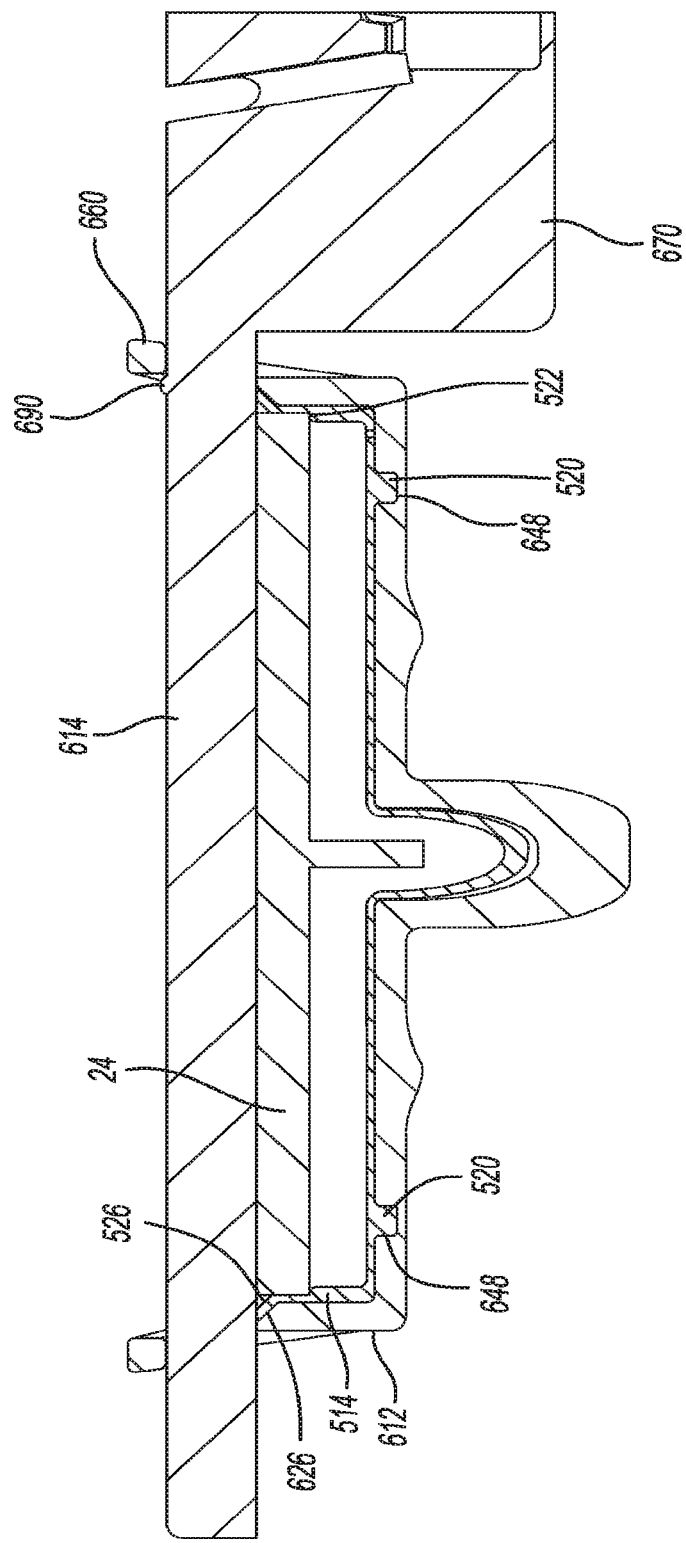
FIG. 20 is a cross-sectional taken along lines 20-20 of FIG. 18.
Figure 21:
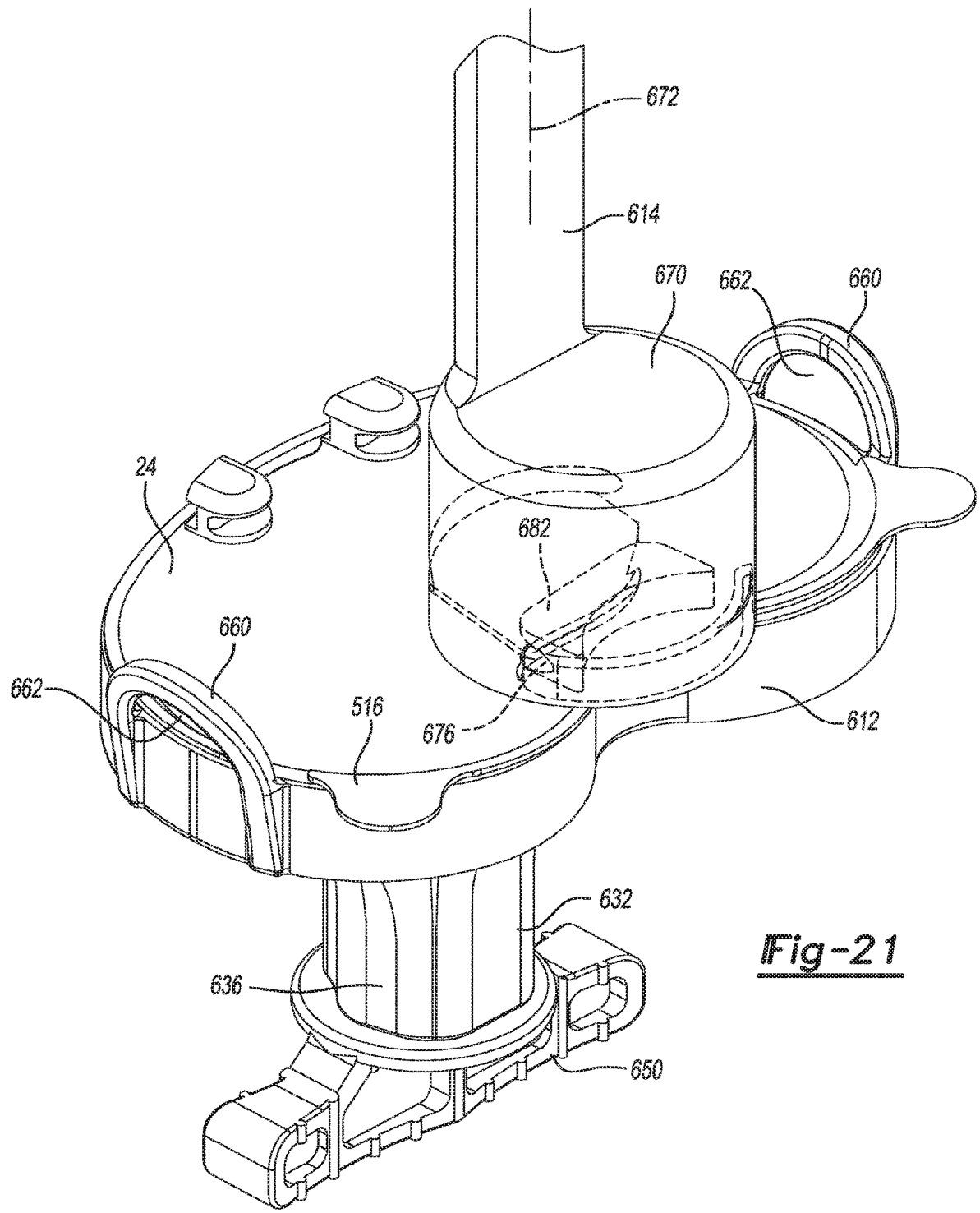
FIG. 21 is a perspective view of the mold and tibial component of FIG. 18 and shown with the locking bar engaged to the tibial component for withdrawal of the tibial component from the mold.
Figure 22:
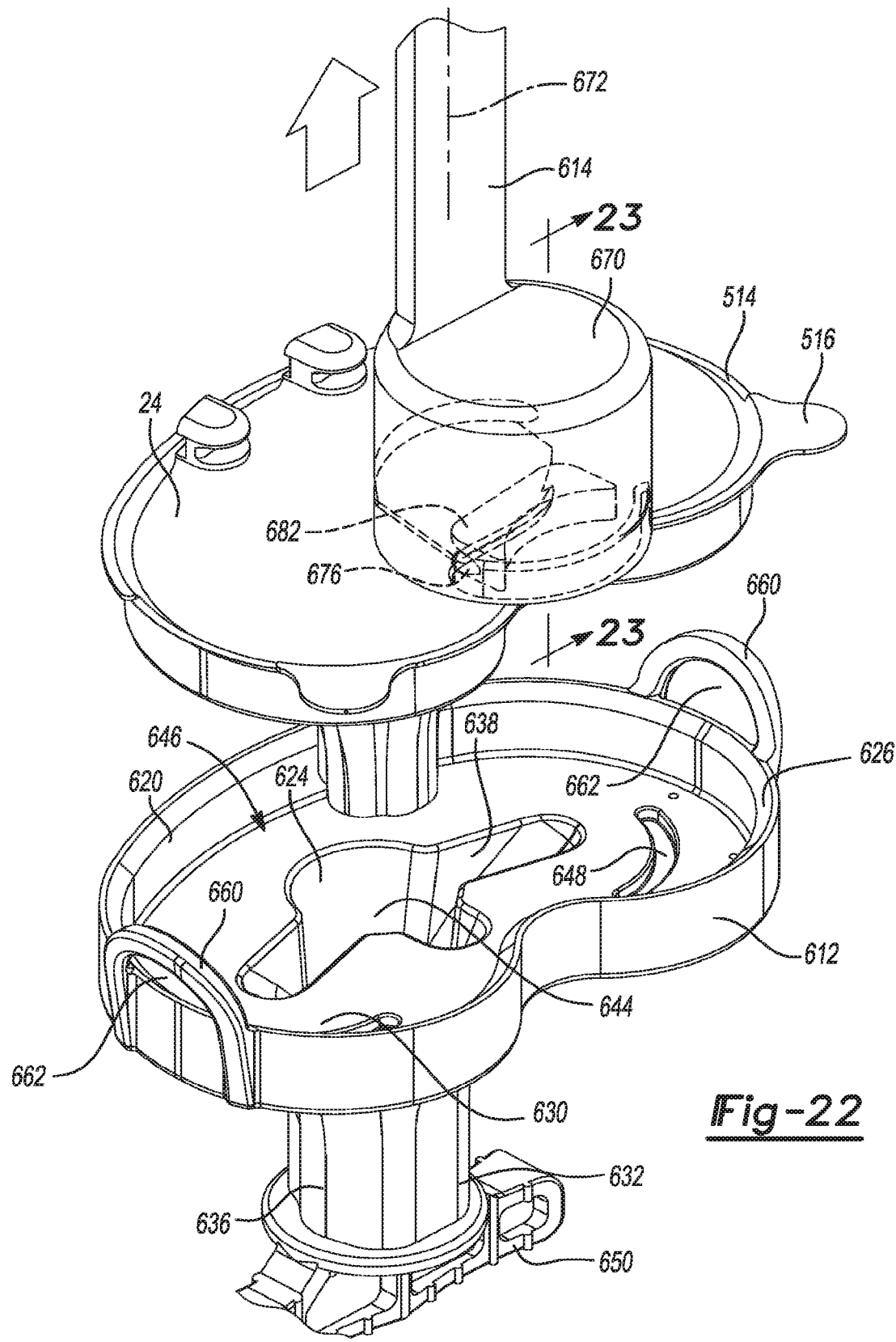
FIG. 22 is a perspective view of the mold, tibial component and locking bar of FIG. 21 and shown subsequent to withdrawal of the tibial tray from the mold.
Figure 23:
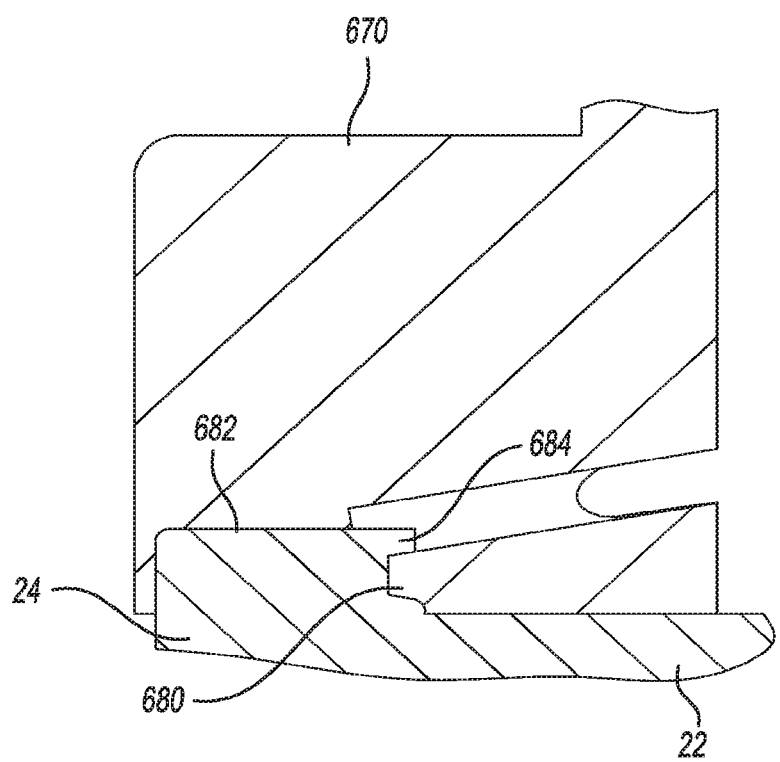
FIG. 23 is a cross-sectional view of the engagement head on the locking bar and posterior tab of the tibial component taken along lines 23-23 of FIG. 22.
Figure 24:
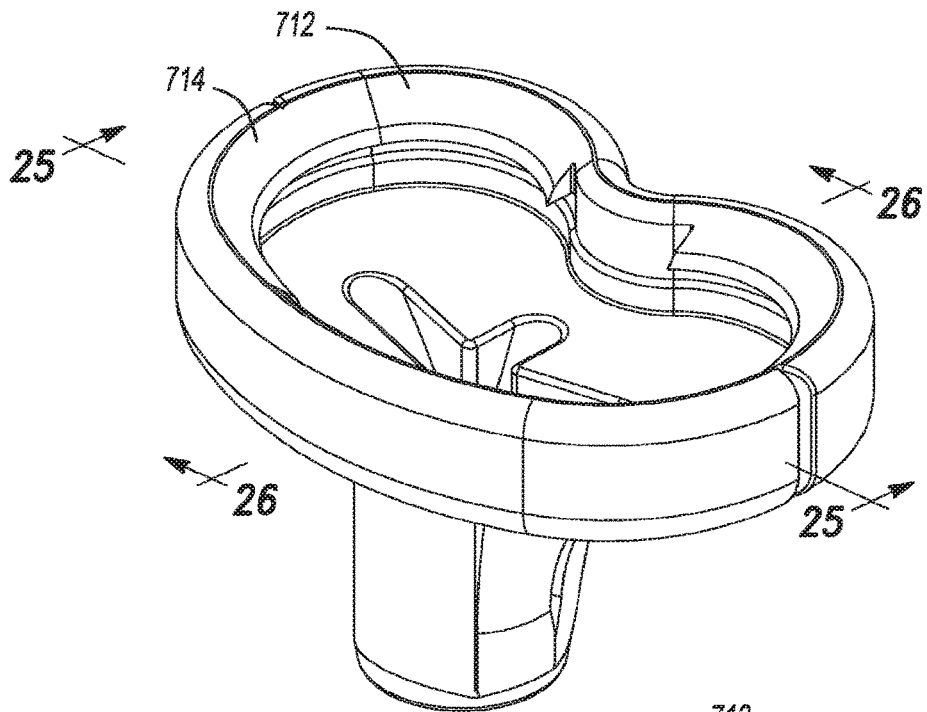
FIG. 24 is a top perspective view of a mold constructed of silicone in accordance to additional features of the present disclosure.
Figure 25:
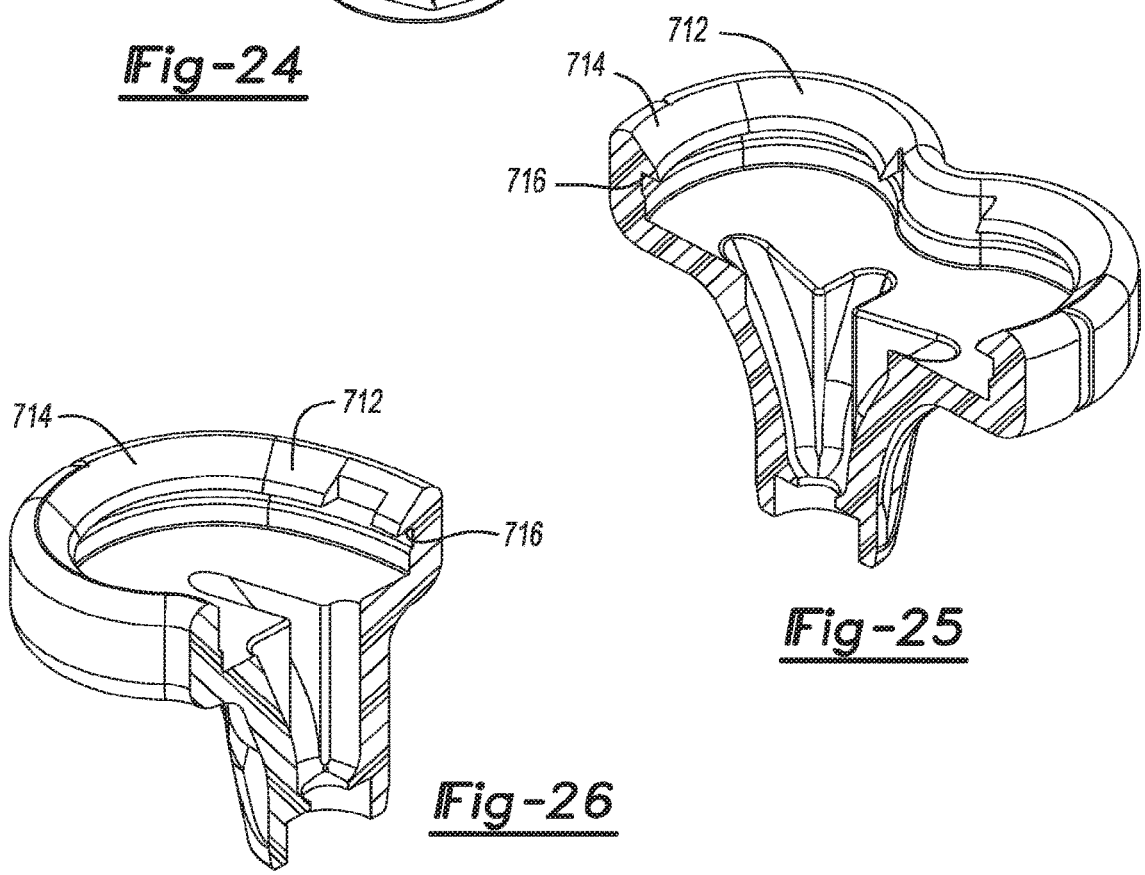
FIG. 25 is a cross-sectional view taken along lines 25-25 of FIG. 24.
Figure 26:
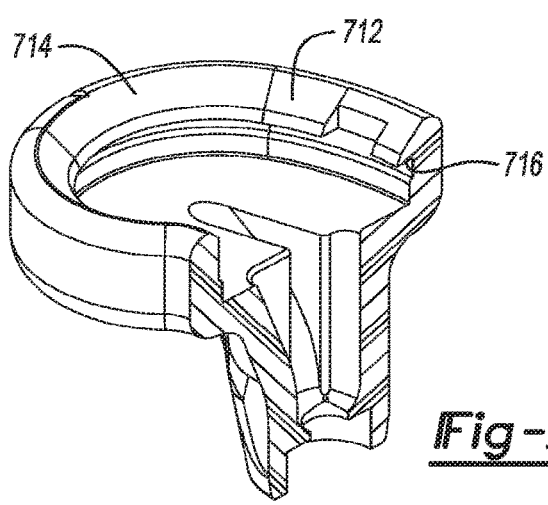
FIG. 26 is a cross-sectional view taken along lines 26-26 of FIG. 24.

It is contemplated that a surgeon can be satisfied once a dough-like structure 28 has sufficiently adhered to the bone opposing surface 70 of the prosthetic implant 22. In other words, after the viscosity of the flowable material 100 has increased and the surface tackiness has decreased to a point that a surgeon could comfortably place and immediately clean up excess flowable material 100 extruded from between the implant 22 and bone during placement of the implant 22, the prosthetic implant 22 and dough-like structure 28 can collectively be removed from the membrane 14 and mold 12. The resultant structure can then be implanted into a tibia 150 as illustrated in FIG. 10.

In other examples, the mold 12 of the kit 20 might function as a part of a sterile packaging of the prosthetic implant 22. Moreover, the kit 20 may also include a shield that could be deployed to inhibit cement contact with a portion of the prosthetic implant 22 which will oppose bone (i.e., the bone opposing surface 70) and/or otherwise may be coated with the flowable material 100. An example of such a shield would be a thin silicone coating/shield/dam that may be slipped over the fins 68 of the stem 66 prior to application of the flowable material 100 to the bone opposing surface 70 of the prosthetic implant 22.

According to features of the instant application, the quality and/or strength of the prosthesis-cement interface is improved via advanced adhesion and micro-interlock through earlier (tackier/lower viscosity) prosthesis-cement contact. The interface quality would also be protected from contamination in several device embodiments. The quality of the cement-bone interface would also benefit according to the teachings of the present disclosure as compared to earlier techniques as the surface of the cement applied to the prosthetic implants prior to placement in the bone are not exposed to air, and thus will not dry out causing a leathery skin to be formed, which is not well-suited to interdigitation with the bone.

Non-limiting Discussion of Terminology:

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

The invention claimed is:

1. A method for forming a flowable material against a prosthetic implant, the method comprising:
    positioning a membrane intermediate an inner surface of a cavity of a mold body and a bone opposing surface of the prosthetic implant, wherein the membrane includes an inlet port extending between an inlet port of the mold body and the cavity of the mold body;
    locating the prosthetic implant at least partially into the cavity of the mold body, thereby creating a void between the bone opposing surface of the prosthetic implant and the inner surface of the cavity;
    introducing the flowable material having a first viscosity into the void and against the bone opposing surface of the prosthetic implant;
    waiting a predetermined amount of time until the flowable material has adhered to the bone opposing surface of the prosthetic implant and has a second viscosity that is higher than the first viscosity; and
    removing the prosthetic implant from the cavity with the flowable material having a dough-like consistency adhered to the bone opposing surface.

2. The method of claim 1, further comprising coupling a flowable material delivery device to the inlet port of the mold body and the inlet port of the membrane.

3. The method of claim 2, further comprising actuating the flowable material delivery device thereby introducing the flowable material having the first viscosity into the void and against the bone opposing surface of the prosthetic implant.

4. The method of claim 3, wherein introducing the flowable material further comprises: releasing air in the void through vent ports formed through the mold body during the introducing of the flowable material.

5. The method of claim 4, wherein introducing the flowable material continues until the flowable material is emitted from at least one vent of the vent ports.

6. The method of claim 3, further comprising peeling the membrane from the flowable material having the second viscosity subsequent to removing the prosthetic implant and the flowable material from the cavity.

7. The method of claim 1, wherein introducing the flowable material comprises introducing bone cement.

8. The method of claim 1, wherein introducing the flowable material having the first viscosity into the void and against the bone opposing surface of the prosthetic implant comprises introducing the flowable material against a bone opposing surface of a tibial component.

9. The method of claim 8, wherein locating the prosthetic implant at least partially into the cavity comprises locating a platform portion of the tibial component into a first cavity portion of the cavity and locating a tibial stem of the tibial component into a second cavity portion of the cavity.

10. A method for forming a flowable material against a prosthetic implant, the method comprising:
    positioning a membrane intermediate an inner surface of a cavity of a mold body and a bone opposing surface of the prosthetic implant, wherein the membrane includes an inlet port extending between an inlet port of the mold body and the cavity of the mold body;
    locating the prosthetic implant at least partially into the cavity of the mold body, thereby creating a void between the bone opposing surface of the prosthetic implant and the inner surface of the cavity;
    introducing the flowable material into the void and against the bone opposing surface of the prosthetic implant; and
    removing the prosthetic implant from the cavity when the flowable material has a dough-like consistency adhered to the bone opposing surface.

11. The method of claim 10, further comprising coupling a flowable material delivery device to the inlet port of the mold body and the inlet port of the membrane.

12. The method of claim 11, further comprising actuating the flowable material delivery device thereby introducing the flowable material having a first viscosity into the void and against the bone opposing surface of the prosthetic implant.

13. The method of claim 12, wherein introducing the flowable material further comprises: releasing air in the void through vent ports formed through the mold body during the introducing of the flowable material.

14. The method of claim 13, wherein introducing the flowable material continues until the flowable material is emitted from at least one vent of the vent ports.

15. The method of claim 10, further comprising peeling the membrane from the flowable material after a change in viscosity of the flowable material and subsequent to removing the prosthetic implant and the flowable material from the cavity.

16. The method of claim 10, wherein introducing the flowable material comprises introducing bone cement.

17. The method of claim 10, wherein introducing the flowable material into the void and against the bone opposing surface of the prosthetic implant comprises introducing the flowable material against a bone opposing surface of a tibial component.

18. The method of claim 17, wherein locating the prosthetic implant at least partially into the cavity comprises locating a platform portion of the tibial component into a first portion of the cavity and locating a tibial stem of the tibial component into a second portion of the cavity.

19. A method for forming a flowable material against a prosthetic implant, the method comprising:
    positioning a membrane intermediate an inner surface of a cavity of a mold body and a bone opposing surface of the prosthetic implant, wherein the membrane includes an inlet port extending between an inlet port of the mold body and the cavity of the mold body via an elongated wall;
    locating the prosthetic implant at least partially into the cavity of the mold body, thereby creating a void between the bone opposing surface of the prosthetic implant and the inner surface of the cavity;
    introducing the flowable material into the void and against the bone opposing surface of the prosthetic implant;
    removing the prosthetic implant from the cavity when the flowable material has a dough-like consistency adhered to the bone opposing surface; and removing the membrane from the flowable material subsequent to removing the prosthetic implant and the flowable material from the cavity.

\* \* \* \* \*